(12) United States Patent
Kamata et al.

(10) Patent No.: US 11,183,809 B2
(45) Date of Patent: Nov. 23, 2021

(54) PASSIVE Q-SWITCH PULSE LASER DEVICE, PROCESSING APPARATUS, AND MEDICAL APPARATUS

(71) Applicant: SONY CORPORATION, Tokyo (JP)

(72) Inventors: Masanao Kamata, Tokyo (JP); Sumito Mizumura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/615,171

(22) PCT Filed: Apr. 24, 2018

(86) PCT No.: PCT/JP2018/016608
§ 371 (c)(1),
(2) Date: Nov. 20, 2019

(87) PCT Pub. No.: WO2018/221083
PCT Pub. Date: Dec. 6, 2018

(65) Prior Publication Data
US 2020/0176946 A1 Jun. 4, 2020

(30) Foreign Application Priority Data
May 29, 2017 (JP) .............................. JP2017-105456

(51) Int. Cl.
*H01S 3/08* (2006.01)
*H01S 3/11* (2006.01)
(Continued)

(52) U.S. Cl.
CPC ............ *H01S 3/1115* (2013.01); *A61F 9/008* (2013.01); *H01S 3/08054* (2013.01); *H01S 3/17* (2013.01);
(Continued)

(58) Field of Classification Search
CPC ............... H01S 3/1115; H01S 3/08054; H01S 3/09415; H01S 3/1611; H01S 3/1643; H01S 3/1118; H01S 3/08059; A61F 9/008
See application file for complete search history.

(56) References Cited

U.S. PATENT DOCUMENTS 4,601,288 A * 7/1986 Myers ................. A61F 9/00736
606/11
6,373,865 B1   4/2002 Nettleton et al.
(Continued)

FOREIGN PATENT DOCUMENTS

AU           3275401 A       8/2001
CN         104577696 A       4/2015
(Continued)

OTHER PUBLICATIONS

Li et al., "Efficient excitations of radially and azimuthally polarized Nd:YAG ceramic microchip laser by use of subwavelength multilayer concentric gratings composed of Nb2O5/SiO2", Optical Society of America, 2008, vol. 16, No. 14, Optics Express (Year: 2008).*

(Continued)

*Primary Examiner* — Tod T Van Roy
(74) *Attorney, Agent, or Firm* — Chip Law Group

(57) ABSTRACT

There is provided a passive Q-switch pulse laser device including a laser medium, and a saturable absorber. The laser medium is disposed between a pair of reflection means included in an optical resonator. The laser medium is excited by specific excitation light to emit emission light. The saturable absorber is disposed on an optical axis of the optical resonator and on a downstream side of the laser medium between the pair of reflection means. The saturable absorber has a transmittance increased by absorption of the emission light. At least one of the pair of reflection means is a polarizing element. The polarizing element has different
(Continued)

reflectances with respect to the respective pieces of emission light in polarization directions orthogonal to each other.

9 Claims, 2 Drawing Sheets

(51) Int. Cl.
  *A61F 9/008* (2006.01)
  *H01S 3/17* (2006.01)
  *A61B 18/20* (2006.01)
  *H01S 3/0941* (2006.01)
  *H01S 3/16* (2006.01)

(52) U.S. Cl.
  CPC . *A61B 2018/20553* (2017.05); *H01S 3/09415* (2013.01); *H01S 3/1611* (2013.01); *H01S 3/1643* (2013.01)

(56) References Cited

U.S. PATENT DOCUMENTS

| | | | |
|---|---|---|---|
| 2002/0097756 | A1 | 7/2002 | Nettleton et al. |
| 2002/0101889 | A1 | 8/2002 | Nettleton et al. |
| 2012/0081769 | A1 | 4/2012 | Dergachev |
| 2014/0369374 | A1* | 12/2014 | Huber ............... H01S 5/183 372/107 |
| 2015/0117475 | A1 | 4/2015 | Taira et al. |
| 2015/0205157 | A1 | 7/2015 | Sakai et al. |
| 2018/0275487 | A1* | 9/2018 | Bhandari ............... H01S 3/109 |

FOREIGN PATENT DOCUMENTS

| | | |
|---|---|---|
| CN | 104755999 A | 7/2015 |
| DE | 102014015813 A1 | 4/2015 |
| JP | 2006-073962 A | 3/2006 |
| JP | 2009-218232 A | 9/2009 |
| JP | 2009-295838 A | 12/2009 |
| JP | 2015-200681 A | 11/2015 |
| JP | 6281935 B2 | 2/2018 |
| WO | 2001/057972 A1 | 8/2001 |
| WO | 2017/060967 A1 | 4/2017 |

OTHER PUBLICATIONS

International Search Report and Written Opinion of PCT Application No. PCT/JP2018/016608, dated Jul. 3, 2018, 09 pages of ISRWO.

Kir'Yanov, et al., Enhancing Type-II Optical Second-Harmonic Generation by the use of a Laser Beam with a Rotating Azimuth of Polarization, Applied Physics Letters, vol. 78, No. 7, Feb. 12, 2001, 05 pages.

Kir'Yanov, et al., Second-Harmonic Generation by Nd3+:YAG/Cr4+:YAG Laser Pulses with Changing State of Polarization, Optical Society of America, Feb. 2000, 04 pages.

Kozawa, et al., "Cylindrical Vector Laser Beam Generated by the Use of a Photonic Crystal Mirror", Applied Physics Express, The Japan Society of Applied Physics, vol. 1, XP055684352, Feb. 1, 2008, 04 pages.

Extended European Search Report of EP Application No. 18810009.3, dated Apr. 21, 2020, 11 pages.

Feng, et al., "Passively Q-Switched Ceramic Nd3+:YAG/Cr4+:YAG lasers", Applied optics, vol. 43, No. 14, XP055684902, May 10, 2004, pp. 2944-2947.

Li, et al., "Radially Polarized and Pulsed Output from Passively Q-switched Nd:YAG Ceramic Microchip Laser", Optics Letters, vol. 33, No. 22, XP055684769, Nov. 15, 2008, pp. 2686-2688.

Office Action for CN Patent Application No. 201880034188.8, dated Mar. 1, 2021, 07 pages of English Translation and 10 pages of Office Action.

Kir'Yanov, et al., "Enhancing type-II optical second-harmonic generation by the use of a laser beam with a rotating azimuth of polarization", Applied Physics Letters, vol. 78, No. 7, Feb. 12, 2001, pp. 874-876.

Kir'Yanov, et al.,"Second-harmonic generation by Nd3+:YAG/Cr4+:YAG laser pulses with changing state of polarization", Journal of the Optical Society of America B, vol. 17. No. 10, Feb. 2000, 04 pages.

Kir'Yanov, et al.,"SHG by a Nd3+:YAG/Cr4+:YAG laser pulse with changing-in-time polarization", Advanced Solid-State Lasers, Feb. 2002, 05 pages.

* cited by examiner

[FIG. 1]
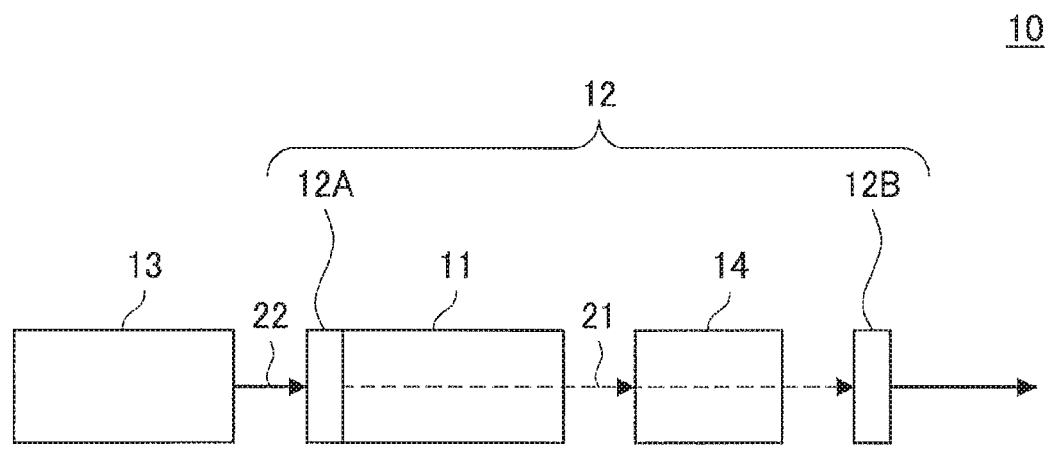
[FIG. 2]
| LASER MEDIUM | SATURABLE ABSORBER |
|---|---|
| Nd:YAG<br>Nd:YVO$_4$<br>Yb:YAG | Cr:YAG<br>SESAM (SEMICONDUCTOR SATURABLE ABSORBER MIRROR) |
| Er GLASS | Co:MALO<br>Co$^{2+}$:LaMgAl<br>U$^{2+}$:CaF$_2$<br>Er$^{3+}$:CaF$_2$ |

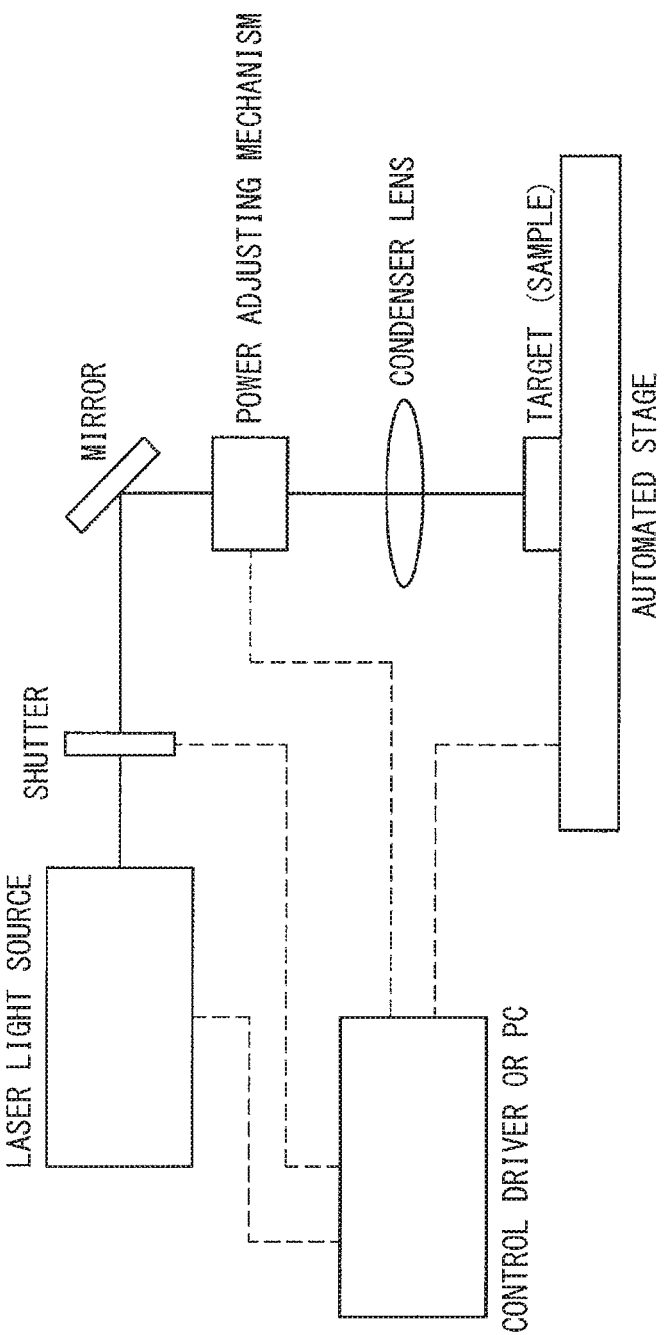
[FIG. 3]

PASSIVE Q-SWITCH PULSE LASER DEVICE, PROCESSING APPARATUS, AND MEDICAL APPARATUS

CROSS REFERENCE TO RELATED APPLICATIONS

This application is a U.S. National Phase of International Patent Application No. PCT/JP2018/016608 filed on Apr. 24, 2018, which claims priority benefit of Japanese Patent Application No. JP 2017-105456 filed in the Japan Patent Office on May 29, 2017. Each of the above-referenced applications is hereby incorporated herein by reference in its entirety.

TECHNICAL FIELD

The present disclosure relates to a passive Q-switch pulse laser device, a processing apparatus, and a medical apparatus.

BACKGROUND ART

In recent years, various laser devices have been developed. For example, a Q-switch pulse laser device has been developed. The Q-switch pulse laser device is a laser device that is able to radiate pulsed laser light having energy at a considerable level or more at predetermined intervals. For example, a passive Q-switch pulse laser device has been actively developed that changes a Q factor with a passive element such as a saturable absorber.

Incidentally, for example, to perform wavelength conversion using a nonlinear optical crystal and shape measurement using linearly polarized light, it is preferable that the polarization direction of laser light given off from a laser device be controlled and stabilized. As a method of controlling the polarization direction of laser light, for example, NPL 1 to 3 below disclose technology of disposing a polarizing element between a laser medium and a saturable absorber in an optical resonator.

However, when the polarizing element is disposed in the optical resonator, the length of the optical resonator increases. This increases the pulse width (i.e., the time width of the pulse increases), decreases the peak intensity of the laser light, or makes it difficult to miniaturize the optical resonator itself or the laser device.

As a method of addressing this problem, for example, PTL 1 below discloses technology of disposing a saturable absorber serving as a crystal having crystallographic axes in three directions in an optical resonator to have different transmittances with respect to the respective pieces of laser emission light in polarization directions orthogonal to each other, thereby causing laser oscillation in a polarization direction along a crystallographic axis in which the transmittance is high.

CITATION LIST

Patent Literature

PTL 1: Japanese Unexamined Patent Application Publication No. 2006-73962

Non-Patent Literature

NPL 1: A. V. Kir'yanov and V. Ablites, "Enhancing type-2 optical second-harmonic generation by the use of a laser beam with a rotating azimuth of polarization" Applied Physics Letters, 12 Feburary 2001, Vol. 78, No. 7, pp. 874 to 876.

NPL 2: Alexander V, Kir'yanov and Vicente Aboites, "Second-harmonics generation by Nd3+: YAG/Cr4+: YAG-laser pulses with chaning state of polarization", J. Opt. Soc. Am. B, October 2000, Vol. 17, No. 10, pp. 1657 to 1664.

NPL 3: A. V. Kir'yanov, J. J. Soto-Bernal, and V. J. Pinto-Robledo, "SHG by a Nd3+: YAG/Cr4+: YAG laser pulse with changing-in-time polaraization", Advanced Solid-State Lasers, 2002, Vol. 68, pp. 88 to 92.

SUMMARY OF THE INVENTION

Problems to be Solved by the Invention

However, in a case where an amorphous material is used as the base material of the laser medium, the generated laser light has optical isotropy and the dependency of the transmittance on crystallographic axes is not obtained. Accordingly, the laser device is unable to control the oscillation polarization direction with the crystallographic axis.

Accordingly, the present disclosure has been devised in view of the above, and an object of the present disclosure is to provide a novel and improved passive Q-switch pulse laser device, processing apparatus, and medical apparatus that are able to generate pulsed laser light having a stable polarization direction while suppressing an increase in the pulse width of the pulsed laser light and a decrease in the peak intensity of the pulsed laser light, and miniaturizing an optical resonator and a laser device in a case where an amorphous material is used as the base material of a laser medium.

Means for Solving the Problems

According to the present disclosure, there is provided a passive Q-switch pulse laser device including: a laser medium; and a saturable absorber. The laser medium is disposed between a pair of reflection means included in an optical resonator. The laser medium is excited by specific excitation light to emit emission light. The saturable absorber is disposed on an optical axis of the optical resonator and on a downstream side of the laser medium between the pair of reflection means. The saturable absorber has a transmittance increased by absorption of the emission light. At least one of the pair of reflection means is a polarizing element. The polarizing element has different reflectances with respect to the respective pieces of emission light in polarization directions orthogonal to each other.

In addition, according to the present disclosure, there is provided a processing apparatus including: a passive Q-switch pulse laser device; and an excitation light source section. The passive Q-switch pulse laser device includes a laser medium, and a saturable absorber. The laser medium is disposed between a pair of reflection means included in an optical resonator. The laser medium is excited by specific excitation light to emit emission light. The saturable absorber is disposed on an optical axis of the optical resonator and on a downstream side of the laser medium between the pair of reflection means. The saturable absorber has a transmittance increased by absorption of the emission light. At least one of the pair of reflection means is a polarizing element. The polarizing element has different reflectances with respect to the respective pieces of emission light in polarization directions orthogonal to each other. The excitation light source section outputs the excitation light. The processing apparatus processes a workpiece with the emission light emitted from the passive Q-switch pulse laser device.

In addition, according to the present disclosure, there is provided a medical apparatus including: a passive Q-switch pulse laser device; and an excitation light source section. The passive Q-switch pulse laser device includes a laser medium, and a saturable absorber. The laser medium is disposed between a pair of reflection means included in an optical resonator. The laser medium is excited by specific excitation light to emit emission light. The saturable absorber is disposed on an optical axis of the optical resonator and on a downstream side of the laser medium between the pair of reflection means. The saturable absorber has a transmittance increased by absorption of the emission light. At least one of the pair of reflection means is a polarizing element. The polarizing element has different reflectances with respect to the respective pieces of emission light in polarization directions orthogonal to each other. The excitation light source section outputs the excitation light. The medical apparatus irradiates a portion of a living body with the emission light emitted from the passive Q-switch pulse laser device.

Effects of the Invention

As described above, according to the present disclosure, it is possible to generate pulsed laser light having a stable polarization direction while suppressing an increase in the pulse width of the pulsed laser light and a decrease in the peak intensity of the pulsed laser light, and miniaturizing an optical resonator and a laser device in a case where an amorphous material is used as the base material of a laser medium.

It should be noted that the above-described effects are not necessarily limitative. Any of the effects indicated in this description or other effects that may be understood from this description may be exerted in addition to the above-described effects or in place of the above-described effects.

BRIEF DESCRIPTION OF DRAWING

FIG. 1 is a diagram illustrating an example of a configuration of a passive Q-switch pulse laser device according to the present embodiment.

FIG. 2 is a table illustrating a combination of a laser medium and a saturable absorber applicable to the passive Q-switch pulse laser device.

FIG. 3 is a diagram illustrating a configuration in a case where the passive Q-switch pulse laser device is applied to a processing apparatus or a medical apparatus.

MODES FOR CARRYING OUT THE INVENTION

The following describes a preferred embodiment of the present disclosure in detail with reference to the accompanying drawings. It should be noted that, in this description and the accompanying drawings, constituent elements that have substantially the same functional configuration are indicated by the same reference signs, and thus redundant description thereof is omitted.

It should be noted that the description is given in the following order.
1. Background
2. Overview of Present Embodiment
3. Configuration of Passive Q-Switch Pulse Laser Device according to Present Embodiment
4. Member Used as Polarizing Element
5. Modification
6. Conclusion

1. BACKGROUND

In recent years, various laser devices have been developed. For example, a Q-switch pulse laser device has been developed. The Q-switch pulse laser device is a laser device that is able to radiate pulsed laser light having energy at a considerable level or more at predetermined intervals. The Q-switch pulse laser device advances pumping while lowering the Q factor of the optical resonator (causing much loss), thereby bringing about a population inversion state. Then, sharply increasing the Q factor when the population inversion state reaches a predetermined level instantaneously causes laser oscillation, and short pulsed laser light having a peak value higher than or equal to a considerable level is given off.

The Q-switch pulse laser device includes an active Q-switch pulse laser device that changes the Q factor with an active element such as an electro-optic modulator, and a passive Q-switch pulse laser device that changes the Q factor with a passive element such as a saturable absorber.

The active Q-switch pulse laser device has a large active element, and is thus unable to shorten the intervals between optical resonators. Accordingly, the active Q-switch pulse laser device is unable to shorten the time width of pulses. In addition, the active Q-switch pulse laser device also has the disadvantage of requiring high voltages to drive the active element.

In contrast, the passive Q-switch pulse laser device is able to overcome the disadvantages of the active Q-switch pulse laser device described above, and thus has been actively developed in recent years.

As the configuration of the passive Q-switch pulse laser device, a configuration in which a saturable absorber is disposed together with a laser medium between a pair of reflection means included in an optical resonator is conceivable. In the configuration, when the emission light from the laser medium enters the saturable absorber, the emission light is absorbed by the saturable absorber. The density of electrons of the saturable absorber in the excitation order gradually increases with the absorption of the emission light. However, when the excitation level is satisfied and the density of electrons at the excitation level is saturated at a certain time point, the saturable absorber becomes transparent. At this time, the Q factor of the optical resonator sharply increases, laser oscillation occurs, and laser light is generated.

Incidentally, for example, to perform wavelength conversion using a nonlinear optical crystal and shape measurement using linearly polarized light, it is preferable that the polarization direction of laser light given off from a laser device be controlled and stabilized. As a method of controlling the polarization direction of laser light, for example, NPL 1 to 3 above disclose technology of disposing a polarizing element between a laser medium and a saturable absorber.

However, when the polarizing element is disposed in the optical resonator, the length of the optical resonator increases. This increases the pulse width (i.e., the time width of the pulse increases), decreases the peak intensity of the laser light, or makes it difficult to miniaturize the optical resonator itself or the laser device.

As a method of addressing this problem, for example, PTL 1 above discloses technology of disposing a saturable absorber serving as a crystal having crystallographic axes in three directions in an optical resonator to have different transmittances with respect to the respective pieces of laser emission light in polarization directions orthogonal to each other, thereby causing laser oscillation in a polarization direction along a crystallographic axis in which the transmittance is high.

However, in a case where an amorphous material is used as the base material of the laser medium, the generated laser light has optical isotropy and the dependency of the transmittance on crystallographic axes is not obtained. Accordingly, the laser device is unable to control, for example, the oscillation polarization direction with the crystallographic axis.

In addition, a laser medium including an amorphous material as the base material has been developed in recent years, and the optical characteristics of the laser light generated by the laser medium have been improved. In addition, a laser medium including an amorphous material as the base material is characteristically easy to increase in area while maintaining a uniform composition.

Accordingly, the discloser of the present application has devised the present technology in view of the circumstances described above. The following describes an embodiment of the present disclosure in detail in the order of "2. Overview of Present Embodiment," "3. Configuration of Passive Q-Switch Pulse Laser Device according to Present Embodiment," "4. Member Used as Polarizing Element," and "5. Modification."

2. OVERVIEW OF PRESENT DISCLOSURE

The background of the present disclosure has been described above. Next, the overview of the present disclosure is described.

The passive Q-switch pulse laser device according to the present embodiment includes a laser medium disposed between a pair of reflection means included in an optical resonator and excited to emit light, and a saturable absorber disposed on the optical axis of the optical resonator and on the downstream side of the laser medium between the pair of reflection means. The saturable absorber absorbs the emission light emitted from the laser medium and has a transmittance increased by the absorption. At least one of the pair of reflection means is a polarizing element. The polarizing element has different reflectances with respect to the respective pieces of emission light in the polarization directions orthogonal to each other.

The reflection means including a polarizing element having a polarization selecting function has different reflectances with respect to the respective pieces of emission light in the orthogonal polarization directions. This causes laser oscillation for the emission light in the polarization direction in which the reflectance is higher. In other words, the polarization direction of the emission light is controlled by the polarizing element, and the laser light having a stable polarization direction is consequently generated.

In the present embodiment, at least one of the pair of reflection means is a polarizing element. This allows the passive Q-switch pulse laser device according to the present embodiment to shorten the length of the optical resonator as compared with the case where the plate-type polarizing element is inserted obliquely between the reflection means like the technology described in NPL 1 to 3 above. As a result, the passive Q-switch pulse laser device according to the present embodiment is able to not only generate pulsed laser light having a stable polarization direction, but also suppress an increase in pulse width and a decrease in peak intensity caused by an increase in the length of the optical resonator, allowing the optical resonator and the laser device to be miniaturized.

It should be noted that the following describes, as an example, a case where the laser medium and the saturable absorber each include an amorphous material as the base material, but this is not limitative. The laser medium or the saturable absorber may each include a crystalline material as appropriate as the base material. It should be noted that, in a case where the laser medium includes a single-crystal material as the base material, both the transmittance dependent on a crystallographic axis and the reflectance of a polarizing element have to be taken into consideration. Laser oscillation occurs in the polarization direction that causes less loss.

3. CONFIGURATION OF PASSIVE Q-SWITCH PULSE LASER DEVICE ACCORDING TO PRESENT EMBODIMENT

The overview of the present embodiment has been described above. Next, with reference to FIG. 1, the configuration of the passive Q-switch pulse laser device according to the present embodiment is described. FIG. 1 is a diagram illustrating an example of the configuration of the passive Q-switch pulse laser device according to the present embodiment.

As illustrated in FIG. 1, a passive Q-switch pulse laser device 10 according to the present embodiment includes a laser medium 11 disposed between a pair of reflection means 12 (illustrated as a reflection means 12A and a reflection means 12B in FIG. 1) included in an optical resonator, and excited to emit emission light 21, an excitation light source section 13 that outputs excitation light 22 for exciting the laser medium 11, and a saturable absorber 14 disposed on the optical axis of the optical resonator and on the downstream side of the laser medium 11 between the pair of reflection means 12. The saturable absorber 14 absorbs the emission light 21 emitted from the laser medium 11 and has a transmittance increased by the absorption. Then, as described above, one of the pair of reflection means 12 according to the present embodiment is a polarizing element having a polarization selecting function.

Here, the excitation light source section 13 emits the excitation light 22 that excites the laser medium 11. More specifically, the excitation light source section 13 is disposed outside the pair of reflection means 12, and emits the excitation light 22 having a wavelength of about 808 [nm] that excites $Nd^{3+}$: YAG ceramics, which is, for example, the laser medium 11. In addition, this specification assumes that the excitation light source section 13 includes a semiconductor laser element that emits the excitation light 22, and an optical system (such as a lens) that causes the excitation light 22 to enter the laser medium 11 via the reflection means 12A.

It should be noted that the excitation light source section 13 may generate the excitation light 22 with an element other than a semiconductor laser element as long as it is possible to emit the excitation light 22 that is able to excite the laser medium 11. In addition, the material used for the excitation light source section 13 may be a crystalline material or an amorphous material. In addition, as long as the excitation light source section 13 allows the excitation light 22 to enter the laser medium 11, the excitation light source section 13 does not have to include an optical system such as a lens.

In addition, as described above, in the present embodiment, at least one of the pair of reflection means 12 is a polarizing element having a polarization selecting function. For example, the reflection means 12A of the pair of reflection means 12 that is provided on the excitation light source section 13 side may be a polarizing element, the reflection means 12B disposed to be opposed to the reflection means 12A may be a polarizing element, or the reflection means 12A and the reflection means 12B may be polarizing elements. It should be noted that this specification describes, as an example, a case where the reflection means 12B is a polarizing element.

The reflection means 12A of the pair of reflection means 12 that is provided on the excitation light source section 13 side is, for example, a mirror that transmits the excitation light 22 having a wavelength of about 808 [nm] emitted from the excitation light source section 13, and reflects the emission light 21 of about 1064 [nm] emitted from the laser medium 11 at a predetermined reflectance. The use of a mirror for the reflection means 12A is merely an example, and the mirror may be changed as appropriate. For example, an element including a dielectric multi-layered film may be used for the reflection means 12A. In a case where a dielectric multi-layered film is used, the thickness of the layers is generally one quarter of the laser oscillation wavelength. The total number of layers amounts to several to several hundred layers, and $SiO_2$, SiN, or the like may be used. It should be noted that the above is an example, and this is not limitative as a working example.

In addition, as described above, the reflection means 12B installed to be opposed to the reflection means 12A is a polarizing element in which the transmittance and reflectance of the emission light 21 differ in accordance with the polarization directions. It should be noted that the member used as the polarizing element according to the present embodiment is not particularly limited. In addition, although it is mainly assumed that linearly polarized light is achieved by the polarizing element according to the present embodiment, this is not limitative. Various polarization states such as circularly polarized light, elliptically polarized light, and radially polarized light may be achieved by the polarizing element according to the present embodiment. The member used as the polarizing element according to the present embodiment is described below in detail.

For example, $Nd^{3+}$: YAG ceramics is used for the laser medium 11, and the laser medium 11 is excited by the excitation light 22 having a wavelength of about 808 [nm]. Then, the laser medium 11 emits light having a wavelength of about 1064 [nm] at the time of transition from the upper order to the lower order. It should be noted that the following refers to the light emitted from the laser medium 11 as emission light 21.

The saturable absorber 14 is a member that includes, for example, $Cr^{4+}$: YAG ceramics, and characteristically decreases the light absorbing rate with light absorption saturated. The saturable absorber 14 functions as a passive Q-switch in the passive Q-switch pulse laser device 10. In other words, the saturable absorber 14 absorbs the emission light 21 once entered by the emission light 21 from the laser medium 11. This absorption causes the transmittance of the saturable absorber 14 to increase. Then, in a case where the density of electrons at the excitation level increases and the excitation level is satisfied, the saturable absorber 14 becomes transparent, thereby increasing the Q factor of the optical resonator to cause laser oscillation.

The saturable absorber 14 according to the present embodiment is disposed between the laser medium 11 and the reflection means 12B as an example. It should be noted that the respective end faces of the saturable absorber 14 and the reflection means 12B in the direction vertical to the optical axis may be bonded to each other. More specifically, the respective end faces of the saturable absorber 14 and the reflection means 12B are bonded to each other by a bonding layer having transparency. The transparency of the bonding layer allows the emission light 21 to pass through the bonding layer and cause laser oscillation appropriately.

Here, any material is used for the bonding layer. For example, the material of the bonding layer may be a photocurable resin or a thermosetting resin, or may be a material such as YAG, sapphire, or diamond having transparency to an oscillation wavelength. In addition, although the bonding layer has any transmittance, it is preferable that the transmittance of the bonding layer be 10% or more with respect to the oscillation wavelength to more efficiently cause laser oscillation.

4. MEMBER USED AS POLARIZING ELEMENT

The configuration of the passive Q-switch pulse laser device 10 according to the present embodiment has been described above. Next, in the present embodiment, a member of a polarizing element used for at least one of the pair of reflection means 12 is described.

As described above, the member used as the polarizing element according to the present embodiment is not particularly limited. For example, as the polarizing element according to the present embodiment, a photonic crystal polarizing element in which a photonic crystal is used, a wire grid polarizing element in which a wire grid is used, or a polarizing element in which the orientation of resin materials is used may be used.

It should be noted that, in a case where the passive Q-switch pulse laser device 10 according to the present embodiment gives off laser light with high power, the electric field amplitude inside the optical resonator is large. In other words, a heavier load is imposed on the polarizing element, and it is thus more preferable to use a polarizing element that may withstand the required power. In this regard, photonic crystals are able to exhibit higher resistance to loads associated with laser oscillation, depending on the material, structure, or the like. In addition, wire grids characteristically absorb the emission light 21, while the photonic crystals do not have such characteristics. This facilitates the photonic crystal polarizing element to achieve higher oscillation efficiency than the wire grid polarizing element does. A case where a photonic crystal polarizing element in which a photonic crystal is used as the polarizing element according to the present embodiment as described above is described as an example.

It should be noted that, to more efficiently cause laser oscillation with respect to the emission light 21 in a desired polarization direction, it is preferable that a difference between the reflectances of the photonic crystal polarizing element be 1[%] or more with respect to the respective pieces of emission light 21 in polarization directions orthogonal to each other. However, this is not limitative. The difference between the reflectances of the photonic crystal polarizing element with respect to the respective pieces of emission light 21 in the polarization directions orthogonal to each other may be changed as appropriate.

In addition, to more efficiently cause laser oscillation and improve resistance, it is preferable that the thickness of each layer of the photonic crystal included in the photonic crystal polarizing element be substantially the same as the wavelength of the emission light 21. However, this is not limitative. The thickness of each layer of the photonic crystal may be changed as appropriate. For example, the thickness of each layer of the photonic crystal may be less (or greater) than the wavelength of the emission light 21 by a predetermined value.

In addition, to more efficiently cause laser oscillation and improve resistance, it is preferable that the number of layers stacked in the photonic crystal be about several cycles to several hundreds of cycles. However, this is not limitative. The number of layers stacked in the photonic crystal may be changed as appropriate.

In addition, as the material of the photonic crystal, for example, $SiO_2$, SiN, Si, $Ta_2O_5$, or the like may be used. However, these are not limitative. The material of the photonic crystal may be changed as appropriate.

It should be noted that such a photonic crystal may be formed by alternately stacking $SiO_2$, Si, $Nb_2O_5$, $Ta_2O_5$, $Al_2O_3$, and the like on a substrate having a periodic structure in advance by vapor deposition or sputtering.

5. MODIFICATION

The members used as polarizing elements have been described above. Next, a modification of the present disclosure is described.

In the embodiment described above, a case where $Nd^{3+}$:YAG ceramics is used as the laser medium 11, and $Cr^{4+}$:YAG ceramics is used as the saturable absorber 14 has been described. However, this is merely an example, and the combination of the laser medium 11 and the saturable absorber 14 may be changed as appropriate.

Then, with reference to FIG. 2, a combination of the laser medium 11 and the saturable absorber 14 that are applicable to the passive Q-switch pulse laser device 10 is described as a modification of the present disclosure. FIG. 2 is a table illustrating a combination of the laser medium 11 and the saturable absorber 14 applicable to the passive Q-switch pulse laser device 10.

As illustrated in FIG. 2, in addition to $Nd^{3+}$:YAG ceramics, for example, Nd:YAG (that emits the emission light 21 having a wavelength of about 1064 [nm]), Nd: $YVO_4$ (that emits the emission light 21 having a wavelength of about 1064 [nm]), or Yb: YAG (that emits the emission light 21 having a wavelength of about 1030 [nm] or 1050 [nm]) may be used for the laser medium 11.

It should be noted that, in a case where Nd: YAG, Nd: $YVO_4$, or Yb: YAG is used as the laser medium 11, Cr: YAG or SESAM (Semiconductor Saturable Absorber Mirror) or the like may be used as the saturable absorber 14.

In addition, Er glass (that emits the emission light 21 having a wavelength of about 1540 [nm]) may be used for the laser medium 11. It should be noted that, in a case where Er glass is used as the laser medium 11, Co: MALO, $Co^{2+}$: LaMgAl, $U^{2+}$: $CaF_2$, $Er^{3+}$: $CaF_2$, or the like may be used as the saturable absorber 14.

6. CONCLUSION

The passive Q-switch pulse laser device 10 according to the present embodiment includes the laser medium 11 disposed between the pair of reflection means 12 included in an optical resonator and excited to emit the emission light 21, and the saturable absorber 14 disposed on the optical axis of the optical resonator and on the downstream side of the laser medium 11 between the pair of reflection means 12. The saturable absorber 14 absorbs the emission light 21 emitted from the laser medium 11 and has a transmittance increased by the absorption. At least one of the pair of reflection means 12 is a polarizing element. This shortens the length of the optical resonator as compared with a case where a polarizing element is inserted between the reflection means 12. Accordingly, the passive Q-switch pulse laser device 10 according to the present embodiment is able to not only generate pulsed laser light having a stable polarization direction, but also suppress an increase in pulse width and a decrease in peak intensity caused by an increase in the length of the optical resonator, allowing the optical resonator and the laser device to be miniaturized.

It should be noted that the passive Q-switch pulse laser device 10 according to the present embodiment may be applied to various apparatuses, systems, and the like. For example, the passive Q-switch pulse laser device 10 according to the present embodiment may be applied to an apparatus used to process metals, semiconductors, dielectrics, resins, living bodies, or the like, an apparatus used for LIDAR (Light Detection and Ranging or Laser Imaging Detection and Ranging), an apparatus used for LIBS (Laser Induced Breakdown Spectroscopy), an apparatus used for intraocular refractive surgery (for example, LASIK or the like), an apparatus used for LIDAR for observing the atmosphere such as depth sensing or aerosol, or the like. It should be noted that an apparatus to which the passive Q-switch pulse laser device 10 according to the present embodiment is applied is not limited to the above.

In a case where the passive Q-switch pulse laser device 10 according to the present embodiment is applied to a processing apparatus or a medical apparatus, it is possible to adopt the configuration in which the passive Q-switch pulse laser device 10 according to the present embodiment is used as a laser light source, a shutter, a mirror, and a power adjusting mechanism are controlled by a control driver, and a target on an automated stage is irradiated by using a condenser lens, for example, as illustrated in FIG. 3.

A preferred embodiment(s) of the present disclosure has/ have been described above in detail with reference to the accompanying drawings, but the technical scope of the present disclosure is not limited to such an embodiment(s). A person skilled in the art may find various alterations and modifications within the scope of the appended claims, and it should be understood that they will naturally come under the technical scope of the present disclosure.

Furthermore, the effects described herein are merely illustrative and exemplary, and not limitative. That is, the technique according to the present disclosure may exert other effects that are apparent to those skilled in the art from the description herein, in addition to the above-described effects or in place of the above-described effects.

It should be noted that the following configurations are also fall within the technical scope of the present disclosure.

(1)

A passive Q-switch pulse laser device including:

a laser medium disposed between a pair of reflection means included in an optical resonator, the laser medium being excited by specific excitation light to emit emission light; and a saturable absorber disposed on an optical axis of the optical resonator and on a downstream side of the laser medium between the pair of reflection means, the saturable absorber having a transmittance increased by absorption of the emission light, at least one of the pair of reflection means being a polarizing element, the polarizing element having different reflectances with respect to the respective pieces of emission light in polarization directions orthogonal to each other.

(2)

The passive Q-switch pulse laser device according to (1), in which the saturable absorber includes an amorphous material.

(3)

The passive Q-switch pulse laser device according to any one of (1) or (2), in which the reflection means disposed on the downstream side of the saturable absorber is the polarizing element, and the polarizing element is bonded to the saturable absorber.

(4)

The passive Q-switch pulse laser device according to (3), including a bonding layer between the polarizing element and the saturable absorber.

(5)

The passive Q-switch pulse laser device according to (4), in which the bonding layer transmits the emission light.

(6)

The passive Q-switch pulse laser device according to any one of (1) to (5), in which the polarizing element includes a photonic crystal having a periodic structure of an inorganic material.

(7)

The passive Q-switch pulse laser device according to any one of (1) to (5), in which the polarizing element includes a wire grid polarizing element.

(8)

The passive Q-switch pulse laser device according to any one of (1) to (5), in which the polarizing element includes a polarizing element in which orientation of resin materials is used.

(9)

A processing apparatus including:
a passive Q-switch pulse laser device including
a laser medium disposed between a pair of reflection means included in an optical resonator, the laser medium being excited by specific excitation light to emit emission light, and
a saturable absorber disposed on an optical axis of the optical resonator and on a downstream side of the laser medium between the pair of reflection means, the saturable absorber having a transmittance increased by absorption of the emission light,
at least one of the pair of reflection means being a polarizing element, the polarizing element having different reflectances with respect to the respective pieces of emission light in polarization directions orthogonal to each other; and
an excitation light source section that outputs the excitation light,
the processing apparatus processing a workpiece with the emission light emitted from the passive Q-switch pulse laser device.

(10)

A medical apparatus including:
a passive Q-switch pulse laser device including
a laser medium disposed between a pair of reflection means included in an optical resonator, the laser medium being excited by specific excitation light to emit emission light, and
a saturable absorber disposed on an optical axis of the optical resonator and on a downstream side of the laser medium between the pair of reflection means, the saturable absorber having a transmittance increased by absorption of the emission light,
at least one of the pair of reflection means being a polarizing element, the polarizing element having different reflectances with respect to the respective pieces of emission light in polarization directions orthogonal to each other; and
an excitation light source section that outputs the excitation light,
the medical apparatus irradiating a portion of a living body with the emission light emitted from the passive Q-switch pulse laser device.

REFERENCE SIGNS LIST

10: Passive Q-switch pulse laser device
11: Laser medium
12: Reflection means
13: Excitation light source section
14: Saturable absorber

The invention claimed is:

1. A passive Q-switch pulse laser device, comprising:
an optical resonator that includes a pair of reflection elements;
a laser medium disposed between the pair of reflection elements, wherein
the laser medium is configured to emit emission light based on excitation of the laser medium by excitation light; and
a saturable absorber on an optical axis of the optical resonator, wherein
the saturable absorber is on a downstream side of the laser medium between the pair of reflection elements,
the saturable absorber a is configured to absorb the emission light,
the absorption of the emission light by the saturable absorber increases transmittance of the saturable absorber,
at least one reflection element of the pair of reflection elements is a polarizing element,
the polarizing element is on a downstream side of the saturable absorber,
the polarizing element is bonded to the saturable absorber,
the polarizing element has a first reflectance with respect to a first piece of the emission light in a first polarization direction,
the polarizing element has a second reflectance with respect to a second piece of the emission light in a second polarization direction,
the first reflectance is different from the second reflectance, and
the first polarization direction is orthogonal to the second polarization direction.

2. The passive Q-switch pulse laser device according to claim 1, wherein the saturable absorber comprises an amorphous material.

3. The passive Q-switch pulse laser device according to claim 1, further comprising a bonding layer between the polarizing element and the saturable absorber.

4. The passive Q-switch pulse laser device according to claim 3, wherein the bonding layer is configured to transmit the emission light.

5. The passive Q-switch pulse laser device according to claim 1, wherein the polarizing element comprises a photonic crystal having a periodic structure of an inorganic material.

6. The passive Q-switch pulse laser device according to claim 1, wherein the polarizing element comprises a wire grid polarizing element.

7. The passive Q-switch pulse laser device according to claim 1, wherein the polarizing element comprises a polarizing element in which orientation of a plurality of resin materials is used.

8. A processing apparatus, comprising:
a passive Q-switch pulse laser device including:
an excitation light source section configured to output excitation light;
an optical resonator that includes a pair of reflection elements;
a laser medium between the pair of reflection elements, wherein
the laser medium is configured to emit first emission light based on excitation of the laser medium by the excitation light; and
a saturable absorber disposed on an optical axis of the optical resonator, wherein
the saturable absorber is on a downstream side of the laser medium between the pair of reflection elements,
the saturable absorber is configured to absorb the first emission light,
the absorption of the first emission light by the saturable absorber increases transmittance of the saturable,
at least one reflection element of the pair of reflection elements is a polarizing element,
the polarizing element is on a downstream side of the saturable absorber,
the polarizing element is bonded to the saturable absorber,
the polarizing element has a first reflectance with respect to a first piece of the first emission light in a first polarization direction,
the polarizing element has a second reflectance with respect to a second piece of the first emission light in a second polarization direction,
the first reflectance is different from the second reflectance,
the first polarization direction is orthogonal to the second polarization direction,
the passive Q-switch pulse laser device is configured to emit second emission light via the polarizing element; and
the processing apparatus is configured to process a workpiece with the second emission light emitted from the passive Q-switch pulse laser device.

9. A medical apparatus, comprising:
a passive Q-switch pulse laser device including:
an excitation light source section configured to output excitation light;
an optical resonator that includes a pair of reflection elements;
a laser medium between the pair of reflection elements, wherein
the laser medium is configured to emit first emission light based on excitation of the laser medium by the excitation light; and
a saturable absorber disposed on an optical axis of the optical resonator, wherein
the saturable absorber is on a downstream side of the laser medium between the pair of reflection elements,
the saturable absorber is configured to absorb the first emission light,
the absorption of the first emission light by the saturable absorber increases transmittance of the saturable absorber,
at least one reflection element of the pair of reflection elements is a polarizing element,
the polarizing element is on a downstream side of the saturable absorber,
the polarizing element is bonded to the saturable absorber,
the polarizing element has a first reflectance with respect to a first piece of the first emission light in a first polarization direction,
the polarizing element has a second reflectance with respect to a second piece of the first emission light in a second polarization direction,
the first reflectance is different from the second reflectance,
the first polarization direction is orthogonal to the second polarization direction,
the passive Q-switch pulse laser device is configured to emit second emission light via the polarizing element; and
the medical apparatus is configured to irradiate a portion of a living body with the second emission light emitted from the passive Q-switch pulse laser device.

* * * * *